(12) United States Patent
Matharu et al.

(10) Patent No.: US 9,918,979 B2
(45) Date of Patent: Mar. 20, 2018

(54) PROCESS OF PREPARING LOW ABUK OXYMORPHONE HYDROCHLORIDE

(71) Applicant: Johnson Matthey Public Limited Company, London (GB)

(72) Inventors: Saroop Matharu, Shirley, MA (US);
Brian Heinrich, Fitchburg, MA (US);
Aniruddh Singh, Acton, MA (US);
Mahmoud Mirmehrabi, Halifax (CA)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/608,544

(22) Filed: Jan. 29, 2015

(65) Prior Publication Data
US 2016/0220560 A1   Aug. 4, 2016

(51) Int. Cl.
*A61K 31/485* (2006.01)
*C07D 489/08* (2006.01)
*A61K 47/10* (2017.01)

(52) U.S. Cl.
CPC ............ *A61K 31/485* (2013.01); *A61K 47/10* (2013.01); *C07D 489/08* (2013.01)

(58) Field of Classification Search
CPC .................................................. A61K 31/485
See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,063,064 A | 12/1977 | Saunders et al. | |
| 4,088,864 A | 5/1978 | Theeuwes et al. | |
| 4,200,098 A | 4/1980 | Ayer et al. | |
| 4,285,987 A | 8/1981 | Ayer et al. | |
| 4,861,598 A | 8/1989 | Oshlack | |
| 4,957,681 A | 9/1990 | Klimesch et al. | |
| 5,215,758 A | 6/1993 | Krishnamurthy | |
| 5,273,760 A | 12/1993 | Oshlack et al. | |
| 5,286,493 A | 2/1994 | Oshlack et al. | |
| 5,324,351 A | 6/1994 | Oshlack et al. | |
| 5,356,467 A | 10/1994 | Oshlack et al. | |
| 5,472,712 A | 12/1995 | Oshlack et al. | |
| 7,276,250 B2 | 10/2007 | Baichwal et al. | |
| 7,851,482 B2 | 12/2010 | Dung et al. | |
| 8,114,383 B2 | 2/2012 | Bartholomilus et al. | |
| 8,144,383 B2 * | 3/2012 | Bartholomaus et al. | G02B 26/004 359/265 |
| 8,563,571 B2 | 10/2013 | Gushurst et al. | |
| 2003/0129234 A1 | 7/2003 | Baichwal et al. | |
| 2012/0022093 A1 | 1/2012 | Gushurst et al. | |
| 2012/0059167 A1 | 3/2012 | Buehler et al. | |

FOREIGN PATENT DOCUMENTS

| | | | | |
|---|---|---|---|---|
| WO | 2005097801 A1 | 10/2005 | | |
| WO | 2008048711 | 4/2008 | | |
| WO | 2008072018 A1 | 6/2008 | | |
| WO | 2012163796 | 12/2012 | | |
| WO | WO 2013188418 A1 * | 12/2013 | ........... | C07D 489/02 |
| WO | WO2013188418 A1 * | 12/2013 | | |
| WO | WO 2015015146 A1 * | 2/2015 | ........... | C07D 489/08 |

OTHER PUBLICATIONS

Drug Enforcement Administration. "Oxymorphone." © Apr. 2013. Available from: <http://www.deadiversion.usdoj.gov/drug_chem_info/oxymorphone.pdf>.*

* cited by examiner

*Primary Examiner* — Noble E Jarrell
*Assistant Examiner* — John S Kenyon
(74) *Attorney, Agent, or Firm* — Shanay M. McCastle (57) ABSTRACT

An improved method for the preparation of the low ABUK oxymorphone hydrochloride is provided. The oxymorphone hydrochloride is produced by hydrogenating a starting material comprising oxymorphone base and 14-hydroxymorphinone in a mixture comprising an alcohol, water and an acid, removing some of the water and adding more alcohol to the mixture.

19 Claims, 4 Drawing Sheets

XRPD pattern of Oxymorphone HCl from 1-Propanol Use without Distillation – Solid Form II

PROCESS OF PREPARING LOW ABUK OXYMORPHONE HYDROCHLORIDE

The present disclosure is directed to improved methods of making oxymorphone hydrochloride.

BACKGROUND OF THE INVENTION

Oxymorphone, generally administered in the form of its hydrochloride salt, is a potent semi-synthetic opiate analgesic. Oxymorphone hydrochloride is indicated for the relief of moderate to severe pain and has been approved for use in the United States since 1959. Oxymorphone hydrochloride is also indicated as a pre-operative medication to alleviate apprehension, maintain anesthesia and as an obstetric analgesic. Additionally, oxymorphone hydrochloride may be used to alleviate pain in patients with dyspnea associated with acute left ventricular failure and pulmonary edema. It can be administered as an injectable solution, suppository, tablet or extended release tablet.

Some crystalline forms of oxymorphone hydrochloride are known. For example, U.S. Pat. No. 8,563,571 describes 10 crystalline forms of oxymorphone hydrochloride, including a commercially produced form of oxymorphone hydrochloride Form A, a sesquihydrate (also referred to herein as oxymorphone hydrochloride Form I). U.S. Pat. No. 7,851,482 describes a hydrated form of oxymorphone hydrochloride having less than 10 ppm of 14-hydroxymorphinone. Other crystalline forms of oxymorphone hydrochloride, including mixtures of forms, are described in, for example, U.S. Pat. No. 7,851,482, U.S. Pat. No. 8,563,571 and WO 2012/163796.

Oxymorphone hydrochloride can be produced by processes that utilize oripavine, a compound derived from opium poppy. Generally, these processes involve oxidizing oripavine to form 14-hydroxymorphinone, an α,β-unsaturated ketone (ABUK), and then converting 14-hydroxymorphinone to oxymorphone base by catalytic hydrogenation. If desired, oxymorphone base can be converted to its hydrochloride salt by suspending or dissolving the base in a solvent or solvent/water mixture (e.g. ethanol and water) and adding hydrochloric acid to the mixture, as described for example in WO2008/048711.

The conversion of 14-hydroxymorphinone to oxymorphone base usually results in some amount of 14-hydroxymorphinone present in the isolated oxymorphone base. Thus, the final oxymorphone hydrochloride salt typically also contains 14-hydroxymorphinone. This is problematic as ABUKs, including 14-hydroxymorphinone, are suspected genotoxic impurities. Accordingly, several processes have been developed to reduce the amount of 14-hydroxymorphinone in oxymorphone hydrochloride salt. For example, US 2012/0059167 describes processes for reducing the concentration of ABUK impurities in morphinan-6-one products by treatment with a sulfur-containing compound. U.S. Pat. No. 7,851,482 describes a method of preparing oxymorphone hydrochloride product containing less than 10 ppm of 14-hydroxymorphinone, which includes hydrogenating oxymorphone hydrochloride in a strongly acidic solvent/water mixture. However, the process described in the '482 patent can result in an oxymorphone hydrochloride product that contains some residual solvent and thus the product must be further dried and then hydrated in a separate step, as described in U.S. Pat. No. 7,851,482, Example 3.2D.

The present invention overcomes this additional processing to directly obtain crystalline oxymorphone hydrochloride Form I.

SUMMARY OF THE INVENTION

The present disclosure is directed to improved methods of making low ABUK (i.e., less than 10 ppm of 14-hydroxymorphinone) oxymorphone hydrochloride, said methods comprising hydrogenating oxymorphone base in a strongly acidic water/alcohol mixture. The present disclosure is further directed to making new solid forms of oxymorphone hydrochloride according to the improved methods described herein.

DETAILED DESCRIPTION OF THE INVENTION

The present disclosure is directed to novel processes for preparing oxymorphone hydrochloride, as herein described in detail. More particularly, the present disclosure is directed to methods of making low ABUK (i.e., less than 10 ppm of 14-hydroxymorphinone) oxymorphone hydrochloride, including crystalline Forms I and II substantially free of any other forms.

In one embodiment, the starting material comprises oxymorphone base and 14-hydroxymorphinone.

The starting material is hydrogenated in a mixture comprising an alcohol, water, and an acid. Preferably the alcohol is 1-propanol, although other alcohols, such as 2-propanol, may be used. Preferably the acid is hydrochloric acid. More preferably, the acid is concentrated hydrochloric acid, although dilute hydrochloric acid or a solution of hydrogen chloride in an alcohol may be used.

After hydrogenating for a period of time, a portion of the alcohol and water is removed by distillation, preferably by vacuum distillation. An alcohol is added to yield low ABUK oxymorphone hydrochloride. Preferably the alcohol is 1-propanol, although other alcohols, such as 2-propanol, may be used.

The reaction temperature is preferably elevated to the reflux temperature of the distillation process, preferably to about 65° C. The reaction is then cooled to about 50° C. and preferably further cooled to about 2-25° C., most preferably 2-5° C.

Examples 1-4 herein provide embodiments of the preparation of low ABUK oxymorphone hydrochloride in accordance with the present disclosure.

The low ABUK oxymorphone hydrochloride disclosed herein may be characterized by one or more of its physical characteristics or properties including, but not limited to, X-ray powder diffraction ("XRPD") peaks. XRPD analysis on representative samples of the low ABUK oxymorphone hydrochloride as herein described is performed using a Bruker D8 Advance instrument equipped with a Cu Kα radiation source (1.54° Angstrom), a 9-position sample holder and a LYNXEYE™ Super Speed Detector. Samples are placed on zero-background, silicon plate holders.

One skilled in the art would recognize that the °2θ values and the relative intensity values are generated by performing a peak search on the measured data and the d-spacing values are calculated by the instrument from the °2θ values using Bragg's equation. One skilled in the art would further recognize that the relative intensity for the measured peaks may vary as a result of sample preparation, orientation and instrument used, for example. A variation of about ±0.2 is not atypical in obtainable 2θ values.

The low ABUK oxymorphone hydrochloride disclosed herein can be incorporated into pharmaceutical dosage forms, e.g., by admixtures of the low ABUK oxymorphone hydrochloride with conventional excipients, i.e., pharmaceutically acceptable organic or Inorganic carrier substances. For oral formulations, the dosage forms can provide a sustained release of the active component. Suitable pharmaceutically acceptable carriers include but are not limited to, alcohols, gum arabic, vegetable oils, benzyl alcohols, polyethylene glycols, gelate, carbohydrates such as lactose, amylose or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, disintegrants, preservatives, stabilizers, wetting agents, emulsifiers, salts for influencing osmotic pressure buffers, colouring, flavouring and/or aromatic substances and the like. The compositions intended for oral use may be prepared according to any method known in the art and such compositions may contain one or more agents selected from the group consisting of inert, non-toxic pharmaceutically acceptable excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent. The oral dosage forms of the present invention may be in the form of tablets (sustained release and/or immediate release), troches, lozenges, powders or granules, hard or soft capsules, microparticles (e.g., microcapsules, microspheres and the like), buccal tablets, solutions, suspensions, etc.

In certain embodiments, the present disclosure provides for a method of treating pain by administering to a human patient the dosage forms described herein.

When the dosage form is oral, the dosage form of the present invention contains from about 1 mg to about 40 mg of the low ABUK oxymorphone hydrochloride. Particularly preferred dosages are about 5 mg, about 10 mg, about 20 mg or about 40 mg however other dosages may be used as well. The low ABUK oxymorphone hydrochloride can also be formulated with suitable pharmaceutically acceptable excipients to provide a sustained release dosage form. Such formulations can be prepared in accordance with, for example, U.S. Pat. No. 7,851,482, U.S. Pat. No. 7,276,250, US 2003/129234 A1 and US 2003/157167 A1.

The low ABUK oxymorphone hydrochloride can be formulated as a sustained release oral formulation in any suitable tablet, coated tablet or multiparticulate formulation known to those skilled in the art. The sustained release dosage form may include a sustained release material that is incorporated into a matrix along with the oxymorphone salt thereof.

The sustained release dosage form may optionally comprise particles containing the low ABUK oxymorphone hydrochloride. In certain embodiments, the particles have a diameter from about 0.1 mm to about 2.5 mm, preferably from about 0.5 mm to about 2 mm. Preferably, the particles are film coated with a material that permits release of the active at a sustained rate in an aqueous medium. The film coat is chosen so as to achieve, in combination with the other stated properties, desired release properties. The sustained release coating formulations of the present invention should preferably be capable of producing a strong, continuous film that is smooth and elegant, capable of supporting pigments and other coating additives, non-toxic, inert, and tack-free.

Coated Beads

In certain embodiments of the present invention a hydrophobic material is used to coat inert pharmaceutical beads such as nu pariel 18/20 beads, and a plurality of the resultant solid sustained release beads may thereafter be placed in a gelatin capsule in an amount sufficient to provide an effective sustained release dose when ingested and contacted by an environmental fluid, e.g., gastric fluid or dissolution media.

The sustained release bead formulations of the present invention slowly release the active component of the present invention, e.g., when ingested and exposed to gastric fluids, and then to intestinal fluids. The sustained release profile of the formulations of the invention can be altered, for example, by varying the amount of overcoating with the hydrophobic material, altering the manner in which a plasticiser is added to the hydrophobic material, by varying the amount of plasticiser relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with the agent(s) of the present invention are prepared, e.g., by dissolving the agent(s) in water and then spraying the solution onto a substrate, for example, nu pariel 18/20 beads, using a Wuster insert. Optionally, additional ingredients are also added prior to coating the beads in order to assist the binding of the active to the beads, and/or to color the solution, etc. For example, a product that includes hydroxypropylmethylcellulose, etc with or without colorant (e.g., Opadry™, commercially available from Colorcon, Inc.) may be added to the solution and the solution mixed (e.g., for about 1 hour) prior to application of the same onto the beads. The resultant coated substrate, in these example beads, may then be optionally overcoated with a barrier agent, to separate the active component(s) from the hydrophobic sustained release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticiser, e.g. triethyl citrate. Preformulated aqueous dispersions of ethylcellulose, such as Aquacoat™ or Surelease™, may be used. If Surelease™ is used, it is not necessary to separately add a plasticiser. Alternatively, pre-formulated aqueous dispersions of acrylic polymers such as Eudragit™ can be used.

The coating solutions of the present invention preferably contain, in addition to the film-former, plasticiser, and solvent system (i.e., water), a colorant to provide elegance and product distinction. Colour may be added to the solution of the therapeutically active agent instead, or in addition to the aqueous dispersion of hydrophobic material. For example, colour may be added to Aquacoat™ via the use of alcohol or propylene glycol based colour dispersions, milled aluminium lakes and opacifiers such as titanium dioxide by adding colour with shear to water soluble polymer solution and then using low shear to the plasticised Aquacoat™. Alternatively, any suitable method of providing colour to the formulations of the present invention may be used. Suitable ingredients for providing colour to the formulation when an aqueous dispersion of an acrylic polymer is used include titanium dioxide and colour pigments, such as iron oxide pigments. The incorporation of pigments, may, however, increase the retard effect of the coating.

Plasticised hydrophobic material may be applied onto the substrate comprising the agent(s) by spraying using any suitable spray equipment known in the art. In a preferred method, a Wurster fluidised-bed system is used in which an air jet, injected from underneath, fluidises the core material and effects drying while the acrylic polymer coating is sprayed on. A sufficient amount of the hydrophobic material to obtain a predetermined sustained release of the agent(s) when the coated substrate is exposed to aqueous solutions, e.g. gastric fluid, may be applied. After coating with the hydrophobic material, a further overcoat of a film-former, such as Opadry™, is optionally applied to the beads. This overcoat is provided, if at all, in order to substantially reduce agglomeration of the beads.

The release of the agent(s) from the sustained release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents, which function as pore-formers may be organic or inorganic, and include materials that can be dissolved, extracted or leached from the coating in an environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those described in, for example, U.S. Pat. No. 3,845,770, U.S. Pat. No. 3,916,899, U.S. Pat. No. 4,063,064 and U.S. Pat. No. 4,088,864.

Matrix Formulations

In other embodiments of the present invention, the sustained release formulation is achieved via a matrix optionally having a sustained release coating as set forth herein. The materials suitable for inclusion in a sustained release matrix may depend on the method used to form the matrix.

For example, a matrix in addition to the low ABUK oxymorphone hydrochloride may include: hydrophilic and/or hydrophobic materials, such as gums, cellulose ethers, acrylic resins, protein derived materials. The list is not meant to be exclusive, any pharmaceutically acceptable hydrophobic material or hydrophilic material which is capable of imparting sustained release of the agent(s) and which melts (or softens to the extent necessary to be extruded) may be used in accordance with the present invention.

Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols. Of these polymers, acrylic polymers, especially Eudragit™. RSPO—the cellulose ethers, especially hydroxyalkylcelluloses and carboxyalkylcelluloses, are preferred. The oral dosage form may contain between 1% and 80% (by weight) of at least one hydrophilic or hydrophobic material.

When the hydrophobic material is a hydrocarbon, the hydrocarbon preferably has a melting point of between 25° C. and 90° C. Of the long chain hydrocarbon materials, fatty (aliphatic) alcohols are preferred. The oral dosage form may contain up to 60% (by weight) of at least one digestible, long chain hydrocarbon.

Preferably, the oral dosage form contains up to 60% (by weight) of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the Invention have a melting point from about 25° C. to about 200° C., preferably from about 45° C. to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax.

For the purposes of the present invention, a wax-like substance is defined as any material that is normally solid at room temperature and has a melting point of from about 25° C. to about 100° C.

Suitable hydrophobic materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° C. and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon.

Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropyl-methylcellulose and, especially, hydroxyethylcellulose. The amount of the at least one hydroxyalkyl cellulose in the present oral dosage form will be determined, inter alia, by the precise rate of oxymorphone hydrochloride release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid oxymorphone release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a (w/w) of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, preferably, polyethylene glycol. The number average molecular weight of the at least one polyalkylene glycol is preferably between 1,000 and 15,000 especially between 1,500 and 12,000.

Another suitable sustained release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a sustained release matrix may also contain suitable quantities of other materials, e.g. diluents, lubricants, binders, granulating aids, colorants, flavorants and glidants that are conventional in the pharmaceutical art.

Matrix Particulates

In order to facilitate the preparation of a solid, sustained release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose, and the low ABUK oxymorphone hydrochloride; (b) mixing the hydroxyalkyl cellulose containing granules with at least one $C_{12}$ to $C_{36}$ aliphatic alcohol; and (c) optionally, compressing and shaping the granules. Preferably, the granules are formed by wet granulating the hydroxyalkyl cellulose granules with water.

In yet other alternative embodiments, a spheronising agent, together with the active component can be spheronised to form spheroids. Microcrystalline cellulose is a preferred spheronising agent. A suitable microcrystalline cellulose is, for example, the material sold as Avicel PH 101 (Trade Mark, FMC Corporation). In such embodiments, in addition to the active ingredient and spheronising agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in, for example, U.S. Pat. No. 4,861,598.

The additional hydrophobic material may comprise one or more water-Insoluble wax-like thermoplastic substances possibly mixed with one or more wax-like thermoplastic substances being less hydrophobic than said one or more water-Insoluble wax-like substances. In order to achieve constant release, the Individual wax-like substances in the formulation should be substantially non-degradable and Insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colourants, flavourings and glidants that are conventional in the pharmaceutical art. The quantities of these additional materials will be sufficient to provide the desired effect to the desired formulation.

In addition to the above ingredients, a sustained release matrix incorporating melt-extruded multiparticulates may also contain suitable quantities of other materials, e.g. diluents, lubricants, binders, granulating aids, colourants, flavourants and glidants that are conventional in the pharmaceutical art in amounts up to about 50% by weight of the particulate if desired.

Specific examples of pharmaceutically acceptable carriers and excipients that may be used to formulate oral dosage forms are described in, for example, the Handbook of Pharmaceutical Excipients, American Pharmaceutical Association (1986).

Melt Extrusion Multiparticulates

The preparation of a suitable melt-extruded matrix according to the present invention may, for example, include the steps of blending the low ABUK oxymorphone hydrochloride together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 mm to about 5 mm and provides sustained release of the therapeutically active agent for a time period of from about 8 hours to about 24 hours.

An optional process for preparing the melt extrusions of the present invention includes directly metering into an extruder a hydrophobic material, the low ABUK oxymorphone hydrochloride, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For the purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 mm to about 12 mm in length and have a diameter of from about 0.1 mm to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronisation step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tabletting equipment using standard techniques. Techniques and compositions for making tablets (compressed and moulded), capsules (hard and soft gelatin) and pills are also described in, for example, Remington's Pharmaceutical Sciences, (Arthur Osol, editor), 1553-1593 (1980).

In yet another preferred embodiment, the extrudate can be shaped into tablets as set forth in, for example, U.S. Pat. No. 4,957,681, described in additional detail above.

Optionally, the sustained release melt-extruded multiparticulate systems or tablets can be coated, or the gelatin capsule containing the multiparticulates can be further coated, with a sustained release coating such as the sustained release coatings described above. Such coatings preferably include a sufficient amount of hydrophobic material to obtain a weight gain level from about 2% to about 30%, although the overcoat may be greater depending upon the desired release rate, among other things.

The melt-extruded unit dosage forms of the present invention may further include combinations of melt-extruded particles before being encapsulated. Furthermore, the unit dosage forms can also include an amount of an immediate release agent for prompt release. The immediate release agent may be incorporated, e.g., as separate pellets within a gelatin capsule, or may be coated on the surface of the multiparticulates after preparation of the dosage forms (e.g., sustained release coating or matrix-based). The unit dosage forms of the present invention may also contain a combination of sustained release beads and matrix multiparticulates to achieve a desired effect.

The sustained release formulations of the present invention preferably slowly release the agent(s), e.g. when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticiser relative to hydrophobic material, by the inclusion of additional ingredients or excipients, by altering the method of manufacture, etc.

In other embodiments of the invention, the melt extruded material is prepared without the inclusion of the low ABUK oxymorphone hydrochloride, which can be added thereafter to the extrudate. Such formulations typically will have the agents blended together with the extruded matrix material, and then the mixture would be tabletted in order to provide a slow release formulation.

Coatings

The dosage forms of the present invention may optionally be coated with one or more materials suitable for the regulation of release or for the protection of the formulation. In one embodiment, coatings are provided to permit either pH-dependent or pH-independent release. A pH-dependent coating serves to release the active in desired areas of the gastro-intestinal (GI) tract, e.g. the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release regardless of pH-changes in the environmental fluid, e.g., the GI tract. It is also possible to formulate compositions that release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the low ABUK oxymorphone hydrochloride thereof is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2% to about 25% of the substrate in order to obtain a desired sustained release profile. Coatings derived from aqueous dispersions are described in detail, for example, U.S. Pat. No. 5,273,760, U.S. Pat. No. 5,286,493, U.S. Pat. No. 5,324,351, U.S. Pat. No. 5,356,467, and U.S. Pat. No. 5,472,712.

Alkylcellulose Polymers

Cellulosic materials and polymers, including alkylcelluloses, provide hydrophobic materials well suited for coating the beads according to the Invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the Invention.

Acrylic Polymers

In other preferred embodiments of the present invention, the hydrophobic material comprising the sustained release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly (methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described as fully polymerised copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings, which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit™ from Rohm Tech, Inc. There are several different types of Eudragit™, for example Eudragit™ E is an example of a methacrylic acid copolymer that swells and dissolves in acidic media. Eudragit™ L is a methacrylic acid copolymer which does not swell at about pH<5.7 and is soluble at about pH>6. Eudragit™ S does not swell at about pH<6.5 and is soluble at about pH>7. Eudragit™ RL and Eudragit™ RS are water swellable, and the amount of water absorbed by these polymers is pH-dependent, however, dosage forms coated with Eudragit™ RL and RS are pH-independent.

In certain preferred embodiments, the acrylic coating comprises a mixture of two acrylic resin lacquers commercially available from Rohm Pharma under the Tradenames Eudragit™ RL30D and Eudragit™ RS30D, respectively. Eudragit™ RL30D and Eudragit™ RS30D are copolymers of acrylic and methacrylic esters with a low content of quaternary ammonium groups, the molar ratio of ammonium groups to the remaining neutral (meth)acrylic esters being 1:20 in Eudragit™ RL30D and 1:40 in Eudragit™ RS30D. The mean molecular weight is about 150,000. The code designations RL (high permeability) and RS (low permeability) refer to the permeability properties of these agents. Eudragit™ RL/RS mixtures are insoluble in water and in digestive fluids. However, coatings formed from the same are swellable and permeable in aqueous solutions and digestive fluids.

The Eudragit™ RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit™ RL, 50% Eudragit™ RL and 50% Eudragit™ RS, or 10% Eudragit™ RL and 90% Eudragit™ RS. Of course, one skilled in the art will recognize that other acrylic polymers may also be used, such as, for example, Eudragit™ L.

Plasticisers

In embodiments of the present invention where the coating comprises an aqueous dispersion of a hydrophobic material, the inclusion of an effective amount of a plasticiser in the aqueous dispersion of hydrophobic material will further improve the physical properties of the sustained release coating. For example, because ethyl-cellulose has a relatively high glass transition temperature and does not form flexible films under normal coating conditions, it is preferable to incorporate a plasticiser into an ethylcellulose coating containing sustained release coating before using the same as a coating material. Generally, the amount of plasticiser included in a coating solution is based on the concentration of the film-former, e.g., most often from about 1 wt % to about 50 wt % of the film-former. Concentration of the plasticiser, however, can only be properly determined after careful experimentation with the particular coating solution and method of application.

Examples of suitable plasticisers for ethylcellulose include water insoluble plasticisers such as dibutyl sebacate, diethyl phthalate, triethyl citrate, tributyl citrate, and triacetin, although it is possible that other water-insoluble plasticisers (such as acetylated monoglycerides, phthalate esters, castor oil, etc.) may be used. Triethyl citrate is an especially preferred plasticiser for the aqueous dispersions of ethyl cellulose of the present invention.

Examples of suitable plasticisers for the acrylic polymers of the present invention include, but are not limited to citric acid esters such as triethyl citrate, tributyl citrate, dibutyl phthalate, and possibly 1,2-propylene glycol. Other plasticisers that have proved to be suitable for enhancing the elasticity of the films formed from acrylic films such as Eudragit™ RL/RS lacquer solutions include polyethylene glycols, propylene glycol, diethyl phthalate, castor oil, and triacetin. Triethyl citrate is an especially preferred plasticiser for the aqueous dispersions of ethyl cellulose of the present invention.

The addition of a small amount of talc may also help reduce the tendency of the aqueous dispersion to stick during processing, and may act as a polishing agent.

Sustained Release Osmotic Dosage Form

Sustained release dosage forms according to the present invention may also be prepared as osmotic dosage formulations. The osmotic dosage forms preferably include a bilayer core comprising a drug layer (containing the low ABUK oxymorphone hydrochloride) and a delivery or push layer, wherein the bilayer core is surrounded by a semipermeable wall and optionally having at least one passageway disposed therein.

The expression "passageway" as used for the purpose of this invention, includes aperture, orifice, bore, pore, porous element through which the low ABUK oxymorphone hydrochloride can be pumped, diffuse or migrate through a fibre, capillary tube, porous overlay, porous insert, microporous member, or porous composition. The passageway can also include a compound that erodes or is leached from the wall in the fluid environment of use to produce at least one passageway. Representative compounds for forming a passageway include erodable poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The dosage form can be manufactured with one or more passageways in spaced-apart relation on one or more surfaces of the dosage form. A passageway and equipment for forming a passageway are described in, for example, U.S. Pat. No. 3,845,770, U.S. Pat. No. 3,916,899, U.S. Pat. No. 4,063,064 and U.S. Pat. No. 4,088,864. Passageways comprising sustained-release dimensions sized, shaped and adapted as a releasing-pore formed by aqueous leaching to provide a releasing-pore of a sustained-release rate are described in, for example, U.S. Pat. No. 4,200,098 and U.S. Pat. No. 4,285,987.

In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_nH_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkyl-cellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as an osmogel), whereby they push the low ABUK oxymorphone hydrochloride thereof from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulphate, lithium phosphate, lithium chloride, sodium phosphate, potassium sulphate, sodium sulphate, potassium phosphate, glucose, fructose and maltose.

The push layer may optionally include a hydroxypropylalkylcellulose possessing a 9,000 to 450,000 number-average molecular weight. The hydroxypropylalkyl-cellulose is represented by a member selected from the group consisting of hydroxypropylmethylcellulose, hydroxypropylethylcellulose, hydroxypropylisopropyl cellulose, hydroxypropylbutylcellulose, and hydroxypropylpentylcellulose.

The push layer optionally may comprise a non-toxic colourant or dye. Examples of colourants or dyes include but are not limited to Food and Drug Administration Colourants (FD&C), such as FD&C No. 1 blue dye, FD&C No. 4 red dye, red ferric oxide, yellow ferric oxide, titanium dioxide, carbon black, and indigo.

The push layer may also optionally comprise an antioxidant to inhibit the oxidation of Ingredients. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain alternative embodiments, the dosage form comprises a homogenous core comprising the low ABUK oxymorphone hydrochloride, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc). The homogenous core is surrounded by a semipermeable wall having a passageway (as defined above) for the release of the low ABUK oxymorphone hydrochloride.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation, semipermeable crosslinked polystyrenes, semipermeable cross-linked poly(sodium styrene sulfonate), semipermeable crosslinked poly(vinylbenzyltrimethyl ammonium chloride) and semipermeable polymers possessing a fluid permeability of $2.5 \times 10^{-8}$ to $2.5 \times 10^{-2}$ (cm$^2$/hr atm) expressed per atmosphere of hydrostatic or osmotic pressure difference across the semipermeable wall. Other polymers useful in the present invention are known in the art including those in, for example, Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder. An example of a binder includes, but is not limited to a therapeutically acceptable vinyl polymer having a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinyl-caprolactone, poly-n-vinyl-5-methyl-2-pyrrolidone, and poly-n-vinylpyrrolidone copolymers with a member selected from the group consisting of vinyl acetate, vinyl alcohol, vinyl chloride, vinyl fluoride, vinyl butyrate, vinyl laureate, and vinyl stearate. Other binders include for example, acacia, starch, gelatin, and hydroxypropylalkylcellulose of 9,200 to 250,000 average molecular weight.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

In certain preferred embodiments, the present invention includes a therapeutic composition comprising an amount of the low ABUK oxymorphone hydrochloride equivalent to 10 to 40 mg oxymorphone hydrochloride, 25 mg to 500 mg of poly(alkylene oxide) having a 150,000 to 500,000 average molecular weight, 1 mg to 50 mg of polyvinylpyrrolidone having a 40,000 average molecular weight, and 0 mg to about 7.5 mg of a lubricant.

Suppositories

The sustained release formulations of the present invention may be formulated as a pharmaceutical suppository for rectal administration comprising a suitable suppository base, and the low ABUK oxymorphone hydrochloride. Preparation of sustained release suppository formulations is described in, for example, U.S. Pat. No. 5,215,758.

Prior to absorption, the drug must be in solution. In the case of suppositories, solution must be preceded by dissolution of the suppository base, or the melting of the base and subsequent partition of the drug from the suppository base into the rectal fluid. The absorption of the drug into the body may be altered by the suppository base. Thus, the particular suppository base to be used in conjunction with a particular drug must be chosen giving consideration to the physical properties of the drug. For example, lipid-soluble drugs will not partition readily into the rectal fluid, but drugs that are only slightly soluble in the lipid base will partition readily into the rectal fluid.

Among the different factors affecting the dissolution time (or release rate) of the drugs are the surface area of the drug substance presented to the dissolution solvent medium, the pH of the solution, the solubility of the substance in the specific solvent medium, and the driving forces of the saturation concentration of dissolved materials in the solvent medium. Generally, factors affecting the absorption of drugs from suppositories administered rectally include suppository vehicle, absorption site pH, drug pKa, degree of ionisation, and lipid solubility.

The suppository base chosen should be compatible with the active of the present invention. Further, the suppository base is preferably non-toxic and non-irritating to mucous membranes, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata™ (types AB, AB, B, BC, BD, BBC, E, BCF, C, D and 299), manufactured by Henkel, and Witepsol™ (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of base (e.g., alginate) and drug used. Generally, the amount of suppository base is from about 20% to about 90% by weight of the total weight of the suppository. Preferably, the amount of suppository base in the suppository is from about 65% to about 80%, by weight of the total weight of the suppository.

The low ABUK oxymorphone hydrochloride can also be formulated with suitable pharmaceutically acceptable excipients to provide an abuse-proof dosage form. As described in U.S. Pat. No. 8,114,383, opiates, which are highly active in combating severe to very severe pain, are frequently used by abusers to induce a state of narcosis or euphoria. In order to make abuse possible, dosage forms such as tablets or capsules are comminuted, for example ground in a mortar, by the abuser, the active ingredient is extracted from the resultant solution, optionally after being filtered through cotton wool or cellulose wadding, and is administered parenterally, in particular intravenously. An additional phenomenon of this kind of administration, in comparison with abusive oral administration, is a further accelerated increase in active ingredient levels giving the abuser the desired effect, namely the "kick" or "rush." This kick is also obtained if the powdered dosage form is administered nasally, i.e. sniffed.

The low ABUK oxymorphone hydrochloride can be formulated as an abuse-proofed, thermoformed dosage form containing, in addition to the low ABUK oxymorphone hydrochloride, at least one synthetic or natural polymer. The use of polymers having a minimum breaking strength (e.g. 500N) means that pulverisation of the dosage form is considerably more difficult using conventional means, so considerably complicating or preventing the subsequent abuse. At least one polymer selected from the group consisting of polymethylene oxide, polyethylene oxide, polypropylene oxide, polyethylene, polypropylene, polyvinyl chloride, polycarbonate, polystyrene, polyacrylate, copolymers thereof, and mixtures of at least two of the stated polymers is preferably used for this purpose. Such formulations can be prepared in accordance with, for example, U.S. Pat. No. 8,114,383.

In order to achieve an adequate breaking strength of the abuse-proofed dosage form, it is possible to also use at least one natural or synthetic wax with a breaking strength of at least 500 N. Carnauba wax and beeswax are particularly preferred. Carnauba wax is very particularly preferred.

The abuse-proofed dosage forms, which comprise, apart from the low ABUK oxymorphone hydrochloride, at least one hardening polymer and optionally at least one wax, may also comprise one or more of the following components (a)-(f) as auxiliary substances:
  (a) at least one substance which irritates the nasal passages and/or pharynx,
  (b) at least one viscosity-increasing agent, which, with the assistance of a necessary minimum quantity of an aqueous liquid, forms a gel with the extract obtained from the dosage form, which gel preferably remains visually distinguishable when introduced into a further quantity of an aqueous liquid,
  (c) at least one antagonist for each of the active ingredients with abuse potential,
  (d) at least one emetic,
  (e) at least one dye as an aversive agent,
  (f) at least one bitter substance.

Components (a) to (f) are additionally each individually suitable for abuse-proofing the dosage form. Accordingly, component (a) is preferably suitable for proofing the dosage form against nasal, oral and/or parenteral, preferably intravenous, abuse, component (b) is preferably suitable for proofing against parenteral, particularly preferably intravenous and/or nasal abuse, component (c) is preferably suitable for proofing against nasal and/or parenteral, particularly preferably intravenous, abuse, component (d) is preferably suitable for proofing against parenteral, particularly preferably intravenous, and/or oral and/or nasal abuse, component (e) is suitable as a visual deterrent against oral or parenteral abuse and component (f) is suitable for proofing against oral or nasal abuse. Combined use according to the invention of at least one of the above-stated components makes it possible still more effectively to prevent abuse of dosage forms according to the Invention.

In another embodiment, the dosage form according to the Invention may comprise the addition of a swellable agent in order to prevent abuse. When water is added to extract the active ingredient, this agent swells and ensures that the filtrate separated from the gel contains only a small quantity of active ingredients. Such formulations can be prepared in accordance with, for example, U.S. Pat. No. 4,070,494.

In another embodiment, the dosage form according to the invention may comprise a multilayer tablet in order to prevent abuse. The tablet contains the active ingredient and at least one gel former, each in different layers. Such formulations can be prepared in accordance with, for example, U.S. Pat. No. 6,309,668.

EXAMPLES

The invention is illustrated by the following examples.

The following examples are set forth to aid in the understanding of the invention, and are not intended and should not be construed to limit in any way the invention set forth in the claims which follow thereafter.

Example 1

Preparation of Oxymorphone Hydrochloride Forms I and II

Figure 1:
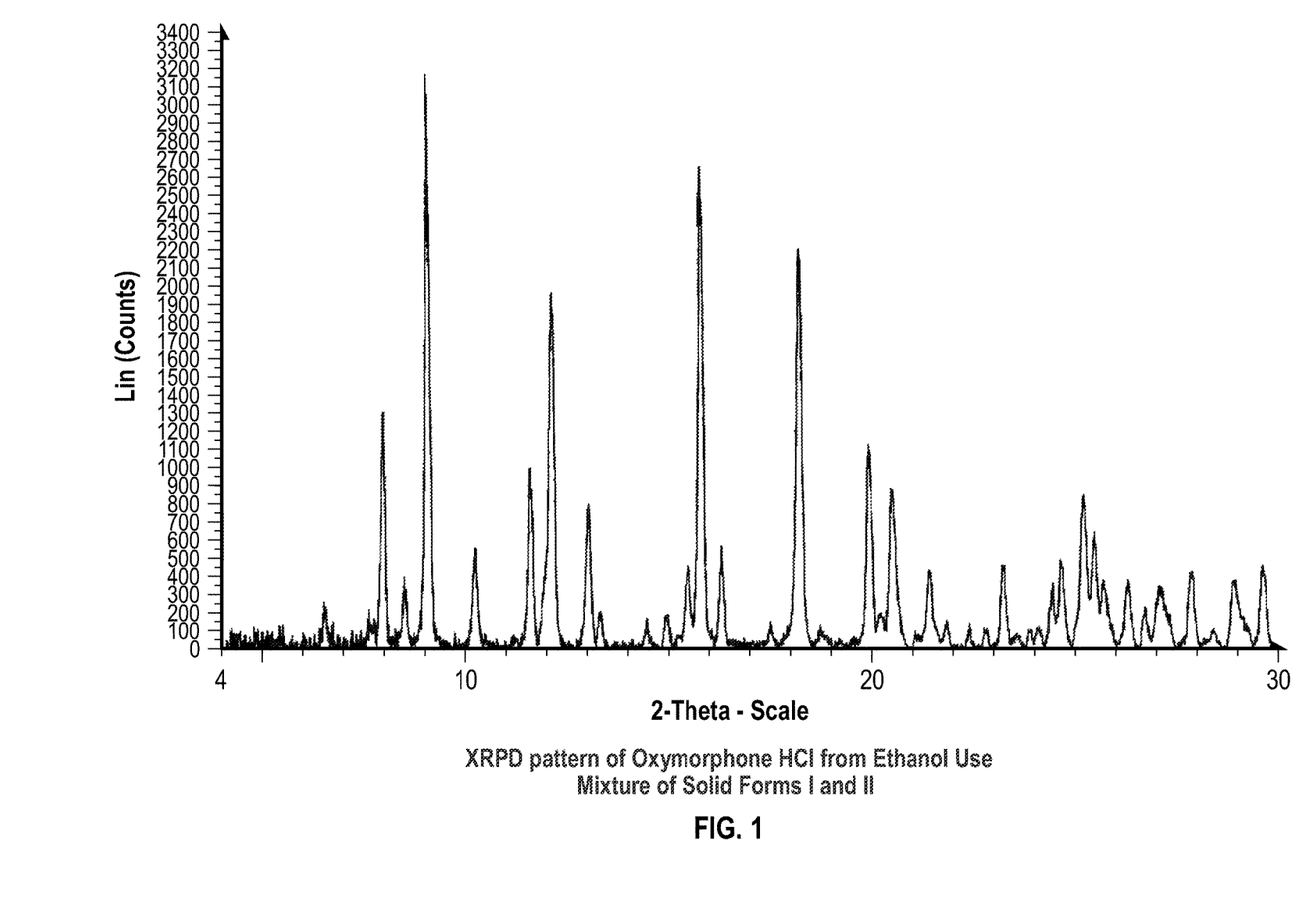
FIG. 1 is an X-ray powder diffractogram of a mixture of oxymorphone hydrochloride Form I and II made in accordance with Example 1 (in terms of °2θ).

About 100 g of oxymorphone base containing about 58 ppm of 14-hydroxymorphinone (by UPLC-MS—select ion monitoring), is added with stirring to a pressure vessel containing about 65.8 g of water and about 204.8 g of ethanol. The resulting slurry is heated to about 60±2° C. and a mixture of 23.9 g of water, about 66 g of concentrated hydrochloric acid, and about 30.6 g of ethanol is charged to give a solution. To the solution is charged about 4 g of 5% Pd/C (4.0 g) under inert gas. The vessel headspace is evacuated using vacuum and backfilled with inert gas. The cycle is repeated twice and subsequent to the final evacuation, the batch temperature is adjusted to about 65±3° C. and the vessel headspace backfilled with hydrogen gas to about 32 psi. The stirred mixture is maintained at about 65±3° C. and about 35±5 psi for about 20 hours. The pressure vessel headspace is replaced with inert gas and the reaction mixture filtered hot using about 8 g of Celite. The reaction vessel is rinsed with about 40 g of ethanol at about 62±3° C. and the rinse filtered and combined with the filtered batch. The hot filtrate is transferred to a vessel, stirred and cooled to about 47° C. and held for about 2 hours. The filtrate is further cooled to about 37° C. and held for about 1 hour to induce crystallization and then to about 0-5° C. and held for about 2 hours. Filtration, followed by drying at about 50° C. under vacuum to constant weight, yields oxymorphone hydrochloride (87.1 g, 77.7% yield, >99.9% area % purity by HPLC analysis; 14-hydroxymorphinone 4 ppm by UPLC-MS—select ion monitoring; mixture of crystalline Forms I and II by XRPD analysis—FIG. 1).

Example 2

Preparation of Oxymorphone Hydrochloride Form II

Figure 2:
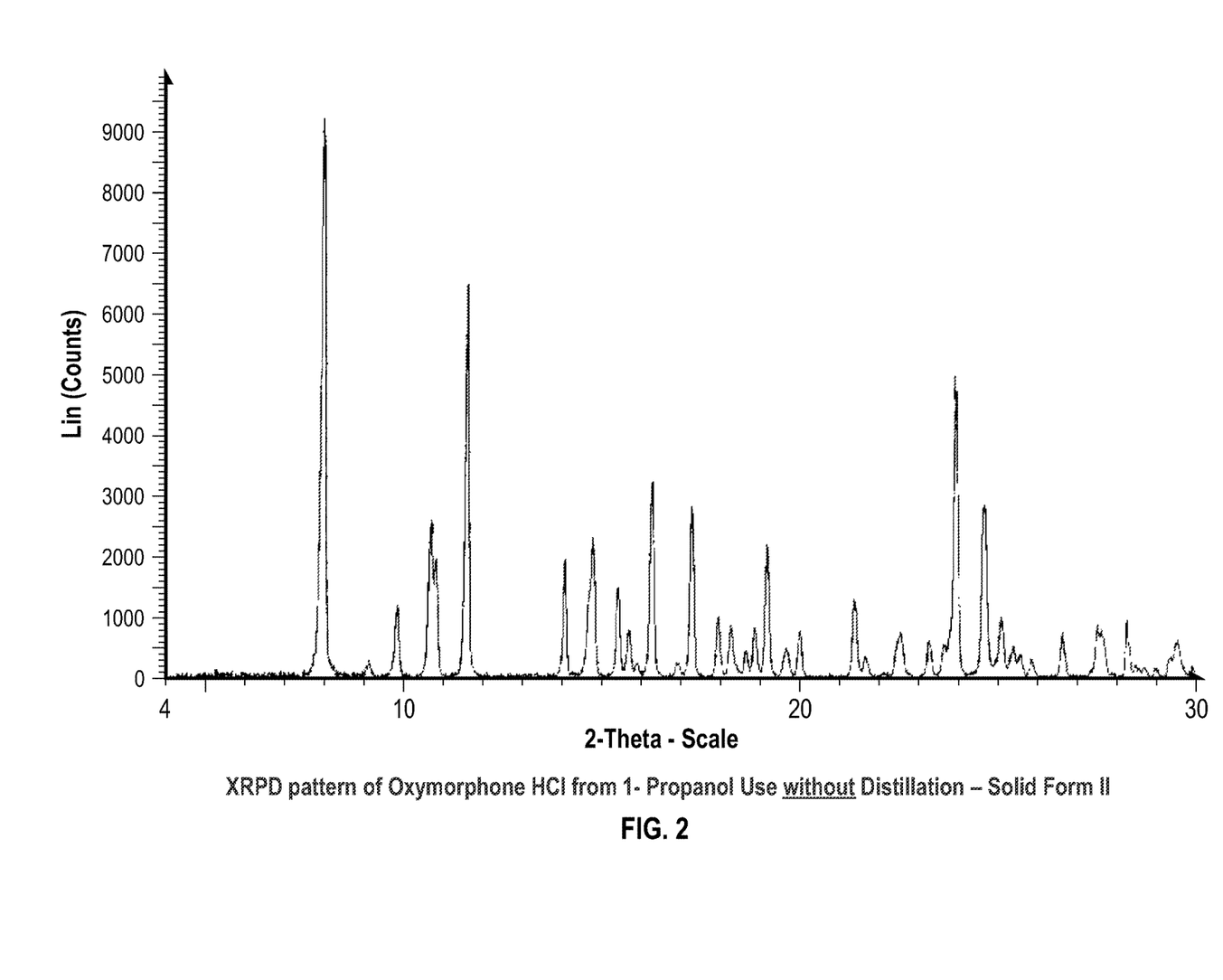
FIG. 2 is an X-ray powder diffractogram of oxymorphone hydrochloride crystalline Form II made in accordance with Example 2 (in terms of °2θ).

About 5 g of oxymorphone base containing about 58 ppm of 14-hydroxymorphinone (by UPLC-MS—select ion monitoring) is added with stirring to a reaction vessel containing about 4.5 g of water and about 11.7 g of 1-propanol. The mixture is heated to about 60±2° C. and about 3.3 g of concentrated hydrochloric acid is added to give a solution. To the solution is charged about 0.2 g of 5% Pd/C under inert gas. The vessel headspace is evacuated using vacuum and backfilled with inert gas. With the reaction vessel under slight vacuum the external vessel temperature is adjusted to about 65±5° C. and hydrogen gas is charged to a pressure reading of about 35-40 psi. The stirred mixture is maintained at about 65±5° C. for about 15 hours. The vessel headspace is replaced with inert gas and the reaction mixture is filtered (>60° C.) through pre-warmed Celite. The reaction vessel is rinsed with about 5 mL of 1-propanol and the rinse is used to wash the Celite pad combining the filtrate with the bulk filtered reaction mixture. The filtrate is transferred to a vessel, as solids begin to crystallize from solution. A sample of the solids is taken for XRPD analysis and found to be crystalline Form II. The batch is reheated to about 65° C. to obtain a solution and cooled slowly to about 45° C. at which time the product starts to crystallize. The mixture is stirred for about 1 hour at this temperature and cooled to about 25° C. and held for about 1 hour. The mixture is cooled to about 0-5° C. and stirred for about 2 hours. The product is isolated by filtration before washing with about 10 mL of cold 1-propanol (about 0-10° C.) and drying for about 12-24 hours at about 40° C. under vacuum to yield oxymorphone hydrochloride (4.0 g, 71.4% yield, >99.9% area % purity by HPLC analysis; crystalline Form II by XRPD analysis—FIG. 2).

Example 3

Preparation of Oxymorphone Hydrochloride Form I

Figure 3:
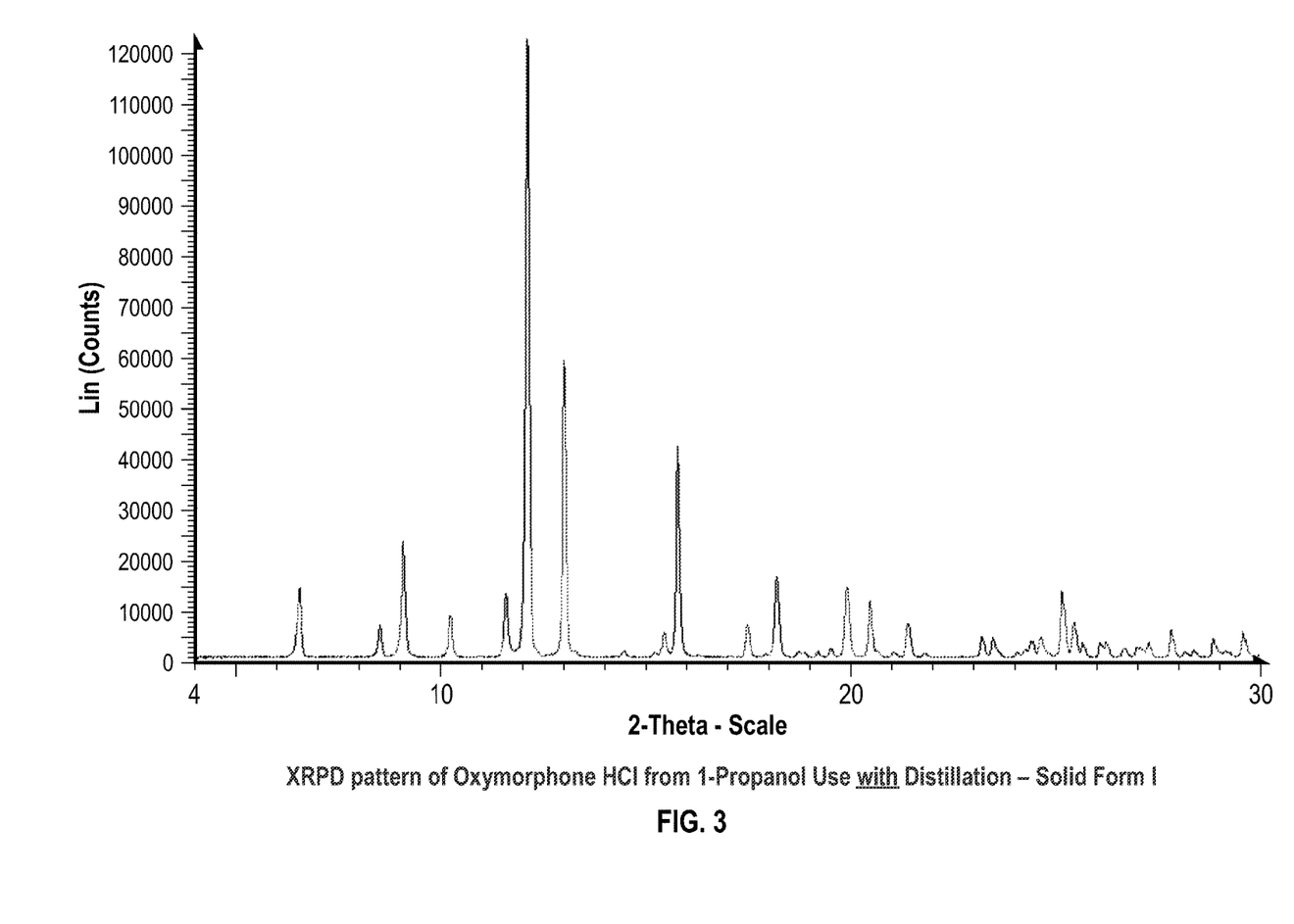
FIG. 3 is an X-ray powder diffractogram of oxymorphone hydrochloride crystalline Form I made in accordance with Example 3 (In terms of °2θ).

About 5 g of oxymorphone base containing about 58 ppm of 14-hydroxymorphinone (by UPLC-MS—select ion monitoring) is charged to a reaction vessel containing about 3.3 g of water and about 11.7 g of 1-propanol. The mixture is heated to about 60±2° C. and a mixture of about 1.2 g of water and about 3.3 g of concentrated hydrochloric acid is added to give a solution. To the solution is charged about 0.2 g of 5% Pd/C under inert gas. The vessel headspace is evacuated using vacuum and backfilled with inert gas. With the reaction vessel under slight vacuum the external vessel temperature is adjusted to about 65±5° C. and hydrogen gas is charged to a pressure reading of about 35-40 psi. The stirred mixture is maintained at about 65±5° C. for about 1 hour. The vessel headspace is replaced with inert gas and the hot reaction mixture filtered through pre-warmed Celite. The reaction vessel is rinsed with about 5 mL of 1-propanol and the rinse is used to wash the Celite pad combining the filtrate with the bulk filtered reaction mixture. The solution is distilled under vacuum to reduce the volumes of solvent from about 5.0 to about 3.5. During the distillation procedure the product starts to crystallize. After the distillation is complete, the vacuum is released and stirring and heating at about 65±5° C. is continued as the slurry is diluted with about 22.1 g of 1-propanol to about 9.0 volumes total solvent volume. Analysis for water content by Karl Fischer titration indicates about 1.96% water present. The slurry is stirred at about 65±5° C. for about 1 hour, then cooled to about 50±5° C. and held for about 1 hour and further cooled to about 0-5° C. and held for about 1 hour. The solid product is isolated by filtration before washing with 1-propanol (2×5.6 g, pre-cooled to 0-5° C.) and drying for about 18 hours under vacuum at about 40° C. to yield oxymorphone hydrochloride (4.15 g, 74.0% yield, >99.9% area % purity by HPLC analysis; crystalline Form I XRPD analysis—FIG. 3).

Example 4

Preparation of Oxymorphone Hydrochloride Form I

Figure 4:
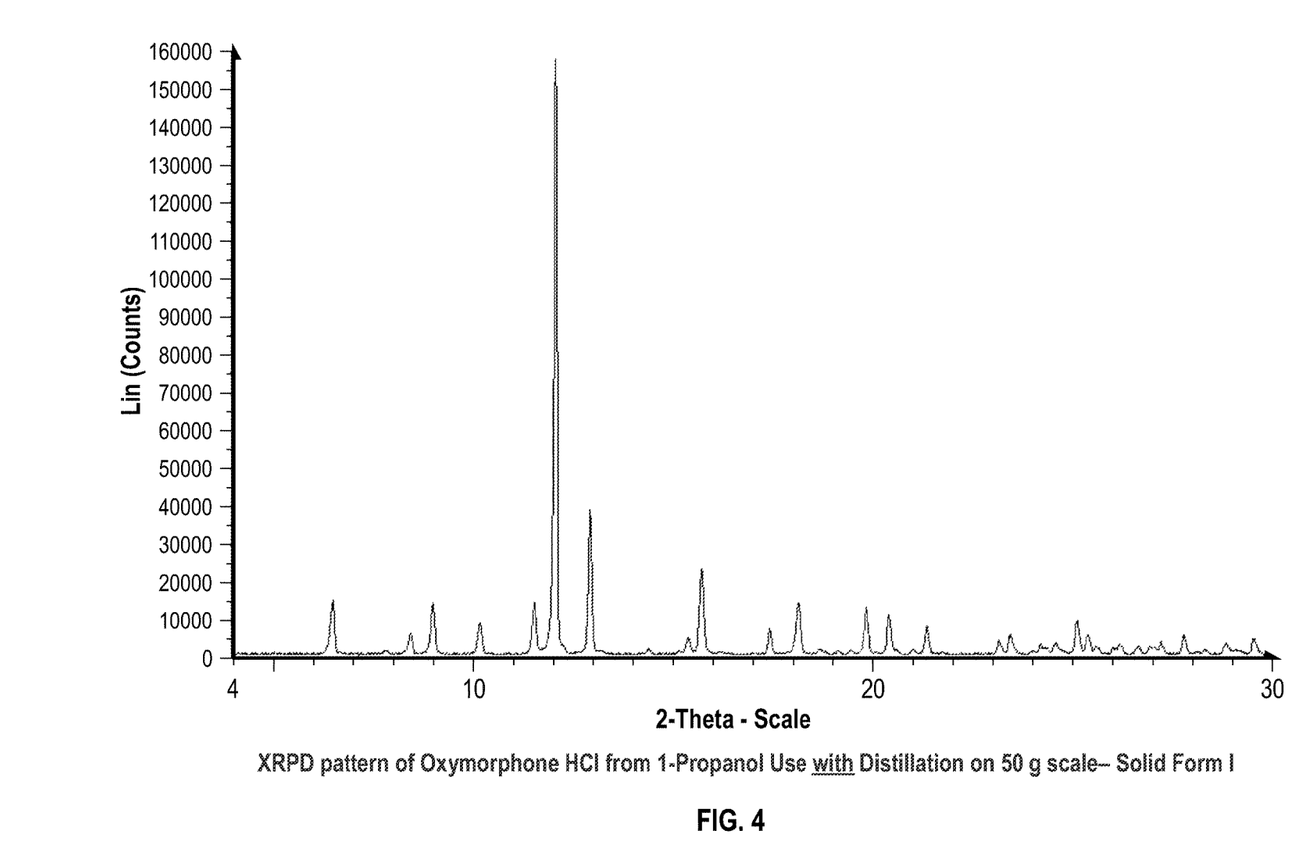
FIG. 4 is an X-ray powder diffractogram of oxymorphone hydrochloride crystalline Form I made in accordance with Example 4 (in terms of °2θ).

About 32.9 g of water, 50.0 g of oxymorphone base containing about 58 ppm of 14-hydroxymorphinone (by UPLC-MS—select ion monitoring) and about 114.7 g of 1-propanol is added with stirring to a pressure vessel. The mixture is heated to 60±2° C. and stirred as a slurry. To this slurry is charged a mixture of about 12.1 g of water, about 33 g of concentrated hydrochloric acid, and about 20 g of 1-propanol to give a solution. To the solution is charged about 2.1 g of 5% Pd/C under inert gas. The vessel headspace is evacuated using vacuum and backfilled with inert gas. The cycle is repeated twice and subsequent to the final evacuation, the batch temperature is adjusted to about 65±3° C. and the vessel headspace backfilled with hydrogen gas to about 40 psi pressure reading. The stirred mixture is then maintained at about 65±3° C. and about 35±5 psi pressure reading for about 20.5 hours. The pressure vessel headspace is replaced with inert gas and the reaction mixture filtered hot through about 4 g of Celite. The reaction vessel is rinsed with about 40 g of 1-propanol at about 65±3° C. and the rinse filtered and combined with the filtered batch. The filtrate solution is heated to about 65±3° C. and distilled under vacuum to reduce the volumes of solvent from about 5.0 to about 3.0-3.5. After the distillation is complete, the vacuum is released and the batch temperature adjusted to about 65±3° C. The solution is diluted with about 221.2 g of 1-propanol to about 9.0 vol. The resulting slurry is stirred at about 65±3° C. for about 2 hours. Analysis for water content by Karl Fischer titration indicated about 8.9% water present. The batch is then cooled to about 50±5° C. and held for about 1.5 hours and further cooled to about 0-5° C. and held for about 1 hour. The solid product is isolated by filtration before washing with 1-propanol (2×56.25 g, pre-cooled to 0-5° C.) and drying for about 18 hours under vacuum at about 40° C. to constant weight to yield oxymorphone hydrochloride (44.2 g, 78.8% yield, >99.9% area % purity by HPLC analysis; 14-hydroxymorphinone 1 ppm by UPLC-MS—select ion monitoring); crystalline Form I by XRPD analysis—FIG. 4).

What is claimed is:

1. A process for preparing an oxymorphone hydrochloride composition having less than 10 ppm of 14-hydroxymorphinone comprising:
   (i) hydrogenating an oxymorphone base composition having more than 10 ppm of 14-hydroxymorphinone in a mixture comprising 1-propanol, water and an acid;
   (ii) removing a portion of the 1-propanol and water in step (i) to reduce the water content of the mixture; and
   (iii) adding alcohol to the mixture.

2. The process of claim 1, wherein the hydrogenating step includes the use of gaseous hydrogen.

3. The process of claim 1, wherein the acid is hydrochloric acid.

4. The process of claim 3, wherein the hydrochloric acid is concentrated hydrochloric acid.

5. The process of claim 3, wherein the hydrochloric acid is diluted hydrochloric acid.

6. The process of claim 1, wherein the acid is a solution of hydrogen chloride in an alcohol.

7. The process of claim 1, wherein the portion of the 1-propanol and water in step (i) is removed by distillation.

8. The process of claim 7, wherein the distillation is under vacuum.

9. The process of claim 1, wherein the process occurs at an elevated temperature.

10. The process of claim 7, wherein the process occurs under reflux.

11. The process of claim 9, wherein the elevated temperature is about 45° C. to about 65° C.

12. The process of claim 1, wherein the water content is reduced to about less than 10% by Karl Fischer titration.

13. The process of claim 1, wherein the oxymorphone hydrochloride is Form I and at least 99.9% pure as measured by HPLC.

14. The process of claim 1, wherein the oxymorphone hydrochloride is Form II and at least 99.9% pure as measured by HPLC.

15. A pharmaceutical formulation comprising at least one pharmaceutically acceptable excipient and oxymorphone hydrochloride according to claim 1.

16. The pharmaceutical formulation according to claim 15, wherein the formulation is a tamper resistant or abuse proof dosage form.

17. The pharmaceutical formulation according to claim 15, wherein the formulation is an extended release or sustained release dosage form.

18. A method of treating pain comprising administering a pharmaceutical formulation according to claim 15 to a patient in need thereof.

19. A process for preparing an oxymorphone hydrochloride composition having less than 10 ppm of 14-hydroxymorphinone comprising:
 (i) hydrogenating an oxymorphone base composition having more than 10 ppm of 14-hydroxymorphinone in a mixture comprising an alcohol, water and an acid;
 (ii) removing a portion of the alcohol and water in step (i) to reduce the water content of the mixture; and
 (iii) adding 1-propanol to the mixture.

* * * * *